United States Patent [19]
Dreitzler et al.

[11] 3,975,942
[45] Aug. 24, 1976

[54] CIRCUIT FOR DETERMINING THE FIRE-NO-FIRE CHARACTERISTICS OF ELECTROEXPLOSIVE DEVICES

[75] Inventors: David R. Dreitzler, Huntsville; Lawrence B. Thorn, Madison, both of Ala.

[73] Assignee: The United States of America as represented by the Secretary of the Army, Washington, D.C.

[22] Filed: June 30, 1975

[21] Appl. No.: 591,927

[52] U.S. Cl. ................................... 73/35; 73/167
[51] Int. Cl.² ......................................... G01N 33/22
[58] Field of Search ............................ 73/35, 167

[56] References Cited
UNITED STATES PATENTS 2,869,364   1/1959   Kabik et al. ............................ 73/167
2,976,485   3/1961   Bartz ...................................... 73/35

*Primary Examiner*—James J. Gill
*Attorney, Agent, or Firm*—Nathan Edelberg; Robert P. Gibson; Jack W. Voigt

[57] ABSTRACT

A circuit for determining the fire no-fire characteristics of electroexplosive devices involves the application of an incrementally adjustable current level automatically to successive electroexplosive devices. The initial predetermined current level is applied to the first electroexplosive device under test. The current level applied to the next and succeeding electroexplosive devices is increased or decreased automatically by a predetermined amount, depending on whether the previous unit functioned or not. This method results in a mean firing current level being obtained with less chance for error and less operator involvement than required by presently established procedures.

5 Claims, 2 Drawing Figures ated, the length of time of application of the current or voltage stimulus is a factor affecting the resulting magnitude of the stimulus at which the device under test will fire. Once determined, it is used to establish the time limit for application of current to the device, if it does not immediately function. The actual firing time is usually recorded in order that the firing delay time can be studied.

CIRCUIT FOR DETERMINING THE FIRE-NO-FIRE CHARACTERISTICS OF ELECTROEXPLOSIVE DEVICES

DEDICATORY CLAUSE

The invention described herein may be manufactured, used, and licensed by or for the Government for Governmental purposes without the payment to us of any royalties thereon.

BACKGROUND OF THE INVENTION

An electroexplosive device (EED) responds to an electrical stimulus and provides an explosive output. For each new type of EED or when a new lot is produced, the device must be characterized. For each type or lot of electroexplosive devices there is an established voltage range or current range within which the devices should fire. The value of stimulus necessary to function or fire an EED such as a hot wire squib is usually determined by means of a go-no-go test such as the established Bruceton procedure. This involves knowing the approximate functioning level and variation of the stimulus, such as current, of the device. In the Bruceton procedure, the first test item has an initial value of current or voltage applied to it. This initial value is determined by the current or voltage setting of a power source. If this test item fires, the power source is manually adjusted to the next lower value of current. This lower value is determined by a previously established estimate covering the spread of current which will fire the device. However, if the device does not fire, the power source setting is manually increased to the next higher level before testing the succeeding device. In addition to the above procedure, the length of time of application of the current or voltage stimulus is a factor affecting the resulting magnitude of the stimulus at which the device under test will fire. Once determined, it is used to establish the time limit for application of current to the device, if it does not immediately function. The actual firing time is usually recorded in order that the firing delay time can be studied.

SUMMARY OF THE INVENTION

This invention is a greatly simplified circuit for performing the Bruceton test. The operator of the test programs the known parameters, such as initial current and incremental current values, into the system control circuits. The test specimens are placed in appropriate receptacles and the sequence is initiated by activating a start switch. The apparatus will automatically perform the Bruceton test, sequentially, on all of the specimens and record all pertinent data. The apparatus allows rapid testing of large numbers of samples with a minimum of operator intervention and human error, and can be used where a device must be tested in such a manner that the stimulus cannot be reapplied if the device does not function (go-no-go device).

DESCRIPTION OF THE PREFERRED EMBODIMENT

Figure 1:
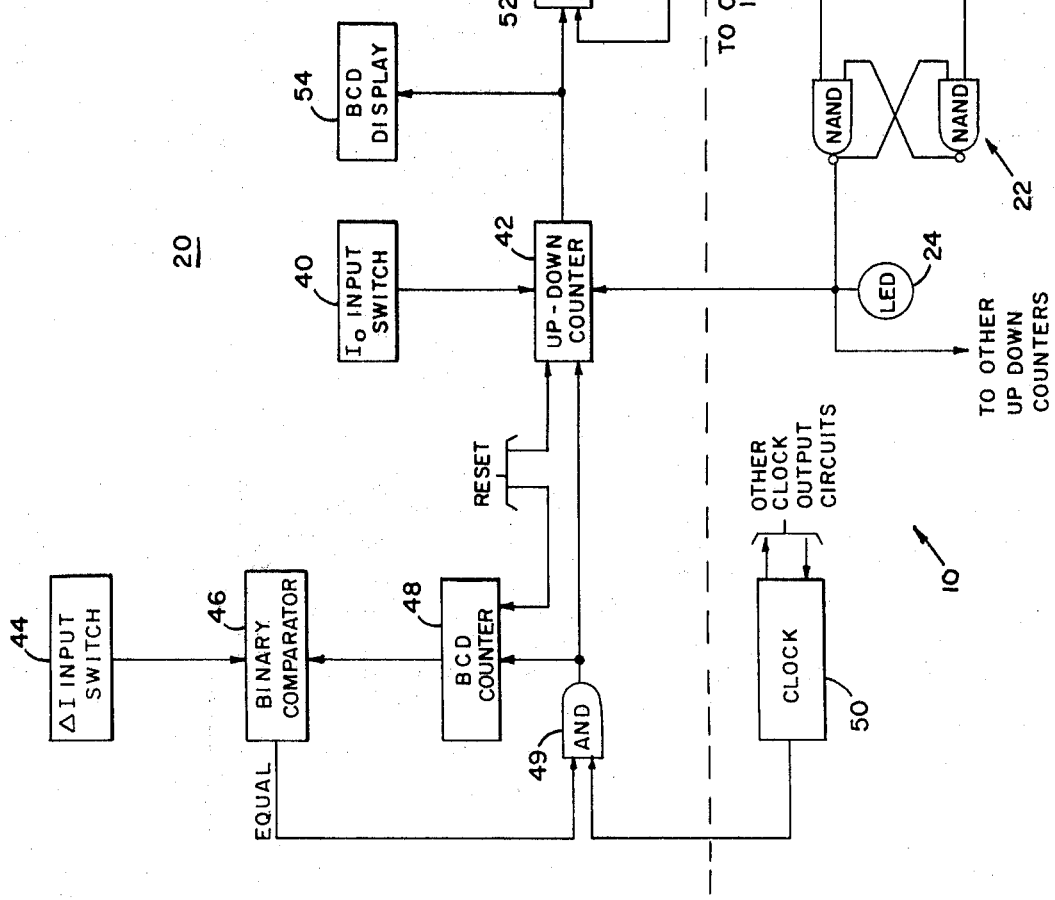
FIG. 1 of the drawing is a simplified block diagram of a preferred embodiment of the inventive apparatus.

A circit is disclosed for obtaining the characteristics of electroexplosive devices (EED) with a minimum of operator intervention and with a minimum of error. As shown in FIG. 1 a simplified block diagram of the testing circuit 10 provides an electrical stimulus signal to an electroexplosive device 12 for determining the characteristics of the EED. A power supply 14 is coupled across the EED for providing a predetermined and variable voltage level or current thereto. A digital-to-analog converter 16 has an output coupled as an input to power supply 14 for controlling the incremental level output of the power supply and for activating the power supply when this output level is to be supplied. A signal representative of a particular voltage or current level is provided from a logic circuit 20 as an input to digital-analog converter 16. Other logic circuit inputs to converter 16 are coupled from a plurality of similar logic circuits 20 (not shown) for each digital signal representative of an incremental value which may be coupled to the power supply 14. A latching circuit 22 provides the add/subtract logic for the system. An output from logic latching circuit 22 is coupled to the logic circuit 20 and to a light emitting diode 24 to indicate whether or not the EED has fired or timed out. To sense a flash when the EED fires a light sensor 26 is positioned adjacent the EED to be fired. An electrical output is coupled from light sensor 26 to latch 22 and an output pulse is coupled to the latch when a flash is sensed by the light sensor. If the EED has not fired after a predetermined time period $t_m$, a clock circuit 28 provides an output pulse to the latch 22 to indicate a nofire condition. A fire command circuit 30 has an output coupled to digital-analog converter 16 and is manually activated to initiate coupling of the converter signal to power supply 14 to test each of the EED squibs. Fire command outputs are also coupled to clock 28 to initiate the clock timing and to a ready light 36 for indicating when each EED is properly positioned for receiving a firing impulse. Inputs to the fire command circuit are coupled from the $t_m$ clock output and from the output of light sensor 26 for responding to either of these output signals to provide an output signal. A reset input allows a pulse to be externally supplied to gate the command circuit.

Each logic circuit 20 comprises an input switch 40 for introducing the binary coded decimal (BCD) equivalent of the anticipated squib firing current $I_o$ into the system. This BCD input current level is coupled into an up-down counter 42. An incremental BCD equivalent current $\Delta I$ input switch 44 has an incremental current output coupled to a binary comparator 46. A BCD counter 48 in each logic circuit is responsive to a variable clock 50 output to provide a variable logical output signal to binary comparator 46 which is compared with the input signal from input switch 44. An AND gate 49 has inputs coupled to receive the output from clock 50 and the output from comparator 46. When the two signals coupled into comparator 46 are unequal, output pulses are coupled from the clock through gate 49 to counters 42 and 48. When the two signal inputs to comparator 46 are equal, an output from the comparator is coupled to AND gate 49 to stop the clock output. The output from comparator 46 closes gate 49 and terminates the pulse chain coupled through gate 49 to counters 42 and 48. An output from up-down counter 42 is coupled as an input to a logic inverter 52 and as an input to BCD display 54. Each logic circuit 20 has an output from a logic inverter 52 coupled to the digital-to-analog converter 16. Each inverter 52 has a gating input coupled from fire command circuit 30 for enabling the inverter. A reset input to each logic circuit 20 allows counters 42 and 48 to be reset to zero after each squib has been tested.

The output from latch 22 is coupled as an input to each up-down counter 42 for each logic circuit 20 with the digital "0" output of the latch representing up and the "1" output representing down. The light emitting diode 24 coupled in common to the latch output circuit indicates whether the squib under test has fired or whether the clock has timed out.

Figure 2:
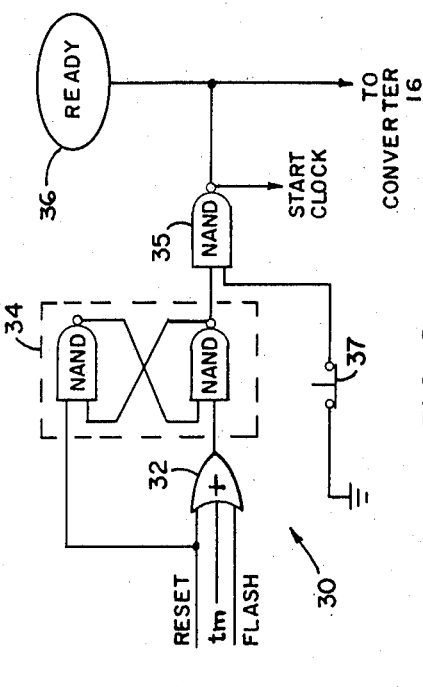
FIG. 2 is a detailed logic circuit for providing the firing command function.

FIG. 2 discloses in detail the fire command circuit 30. An OR gate 32 is coupled to receive the $t_m$ and flash inputs from clock 28 and photocell 26 respectively. The reset input activated by the system operator is also coupled to gate 32. A NAND gate latch 34 has the reset input thereof coupled to the reset input of gate 32 and the set input coupled to the output of gate 32. The output of latch 34 is coupled as an input to NAND gate 35. A system ground is coupled through a normally closed firing switch 37 to the other input of gate 35. When switch 37 is momentarily opened, the state of gate 35 is changed from 1 to 0 for providing an output signal to activate converter 16, logic inverter 52, clock 28 and ready lamp 36. Fire command circuit 30 provides the logic necessary to inhibit converter 16. Therefore no output is coupled to power supply 14 until it is desired to fire a squib. Another squib can be fired when either clock 28 has timed out (no-fire), or the device has fired as indicated by photocell 26 and the firing switch 37 has been depressed.

Logic inverter 52 is a controlled inverter, being enabled by fire command circuit 30. The output is a logical 1 until enabled, it is then inverted. This prevents a current from being inadvertently applied to squib 12 before the firing command is given.

During testing the quantity of EED squibs being tested are fixedly disposed in a squib mount or holding apparatus so that they can be advanced an incremental distance to bring the electrical contact terminals 13a and 13b of each squib 12 into electrical contact with the output terminals of power supply 14. This positioning is accomplished manually or automatically. Before testing, initial digital values are entered for the basic current $I_o$. These values are introduced into the system through input switches 40. The digital values for incremental current $\Delta I$ are introduced into the system by input switches 44. The maximum time delay $t_m$ that each unfired squib 12 is subjected to the output voltage from power supply 14 is established and set into clock 28. The quantity of EED squibs to be tested are loaded in the squib fixture and the squibs are advanced until the first squib 12 is in contact with the output terminals of power supply 14 and in position for light sensor 26 to sense the flash of the squib firing element.

In operation, switches 40 and 44 are loaded to provide a predetermined BCD ouput, the first squib is positioned in electrical contact with the power supply output, the initial state of latch 22 provides either an add or subtract logical output to counters 42, and the counters are set to zero to initiate operation of the logic circuits. The output signal from $\Delta I$ input switch 44 is coupled to comparator 46 where it is compared with the output signal from BCD counter 48. Logic level output of counter 48 is controlled by clock 50. Comparator 46 will produce an output only when the logic levels produced by switch 44 and counter 48 are equal. When this coincidence occurs, an output from comparator 46 closes gate 49 which stops the output pulses coupled from clock 50 through gate 49, thereby stopping the pulse train to updown counter 42 and counter 48. The train of pulses coupled from clock 50 to counter 42 equals the switch setting for $\Delta I$ input switch 44. The initial BCD value of current, $I_o$, is parallel loaded into up-down counter 42 wherein the value of $\Delta I$ is added or subtracted from $I_o$ in response to the logic state of latch 22 to produce the desired BCD output from counter 42. This BCD output is coupled to display circuit 54 where it is recorded to indicate the specific current supplied to squib 12. The output from counter 42 is also coupled to logic inverter 52 where it is coupled out of logic circuit 20 to digital-analog converter 16 for activating power supply 14.

For the first squib under test, fire command circuit 30 is activated by a reset input which the test operator initiates. For succeeding squibs the fire command circuit is preset by the $t_m$ or flash inputs. The test operator then activates a fire switch within circuit 30 which gates converter 16 and allows the power supply 14 output incremental voltage to be impressed across the squib. At this time an output from fire control circuit 30 also starts clock 28 and activates the ready lamp to indicate start of the test.

When squib 12 fires, light is sensed by light sensor 26. Latch 22 is set by the output from sensor 26 when it senses that the EED has fired. If the EED fires, latch 22 is set to provide a logical 1 output which tells up-down counters 42 to subtract from $I_o$ the $\Delta I$ value to produce the desired BCD output signal. If the squib 12 has not functioned after a predetermined time $t_m$ clock 28 will time out and reset the latch. This results in logical 0 output from the latch and this signal is applied to up-down counters 42 to cause the counters to count up by the incremental amount of $\Delta I$. The counters are now set to the new BCD current level which is coupled to respective inverters 52; and the next squib is advanced for testing. Activating fire switch 37 then starts test of the next squib. Each squib is subjected to only one current level, either until it fires or until clock 28 times out, in accordance with established Bruceton testing procedures. When a squib is subjected to a current which does not fire that squib, the squib characteristics are altered by the current making any additional testing of that squib meaningless.

Typically, with a clock rate of 100 kHz, it requires 10 microseconds per count, resulting in a maximum add-/subtract time of 1 millisecond for a 100 hundred count add or subtract signal. This method can be extended to additional decimal digits by using a ripple carry output provided by up-down counter 42. These digits can be multiplexed if the part count is crucial, if not the additional digits can function in parallel. A circuit for determining the fire-no-fire characteristics of the electroexplosive devices can be operated using components such as:

| | |
|---|---|
| Input switches 40 and 44 | Digitran No. 29010 |
| Comparator 46 | Texas Instruments SN7485 |
| Counter 48 | Texas Instruments SN7490 |
| Clocks 50 and 28 | Xrexar Integrated Systems 220M |
| Up-down counter 42 | Texas Instruments SN74190 |
| Display 54 | Hewlett-Packard 5082-7300 |
| Inverter 52 | Texas Instruments 7405 |

| | |
|---|---|
| Converter 16 | Kepco DPD-7-10A |
| Power supply 14 | Kepco OPS-36 |

Although a particular embodiment and form of this invention has been illustrated, it is obvious to those skilled in the art that modifications may be made without departing from the scope and spirit of the foregoing disclosure. For example counters 42 and 48 may be manually set to zero after each squib is tested or they may be reset automatically, as by an output from latch 22 or clock 28 gating the counter reset, or by a monostable multivibrator through contact closure. Similarly, a printer may be coupled to the system to record the firing time or time out of clock 28. Therefore it is understood that the invention is limited only by the claims appended hereto.

We claim:

1. Apparatus for determining the fire-no-fire characteristics of electroexplosive devices, comprising: a power supply for coupling an adjustable current to said electroexplosive device for a predetermined maximum time; a digital-analog converter having an output coupled to said power supply for operating said supply; a logic circuit for coupling a variable logic level signal to said converter; a firing circuit coupled to said converter for initiating operation of said converter; a latching circuit having an output coupled to said logic circuit and first and second inputs; means adjacent said electroexplosive device for sensing optical energy when said device is activated, said means having an output coupled to a first of said latching circuit inputs; and a first clock for coupling an output signal to said second latching circuit input after a predetermined time lapse.

2. Apparatus as set forth in claim 1 wherein said logic circuit comprises an up-down counter having first, second and third inputs and an output, a first binary coded decimal input switch coupled to the first input of said counter for coupling a logic signal thereto indicative of the fundamental current output to be provided from said power source, a second binary coded decimal input switch coupled to said second input of said counter for providing a signal indicative of incremental changes to the power supply fundamental current, the output of said latching circuit being coupled to the third input of said counter for controlling the up-down response of said counter, and a logic inverter having an input coupled to the output of said up-down counter and an output coupled to said digital-analog converter.

3. Apparatus as set forth in claim 2 and further comprising a binary comparator having first and second inputs and an output, said first input being coupled to the output of said incremental input switch; a binary coded decimal counter having an input and an output, the output of said counter being coupled as a second input to said comparator; a second clock having a variable output for providing a variable pulse train; an AND gate having first and second inputs and an output, said first input being coupled to said clock output, the output being coupled as an input to said up-down counter and said binary coded decimal counter, and said second input being coupled to the output of said binary comparator, said binary comparator output being for opening said AND gate and stopping the clock pulse train when the input logic from said incremental current switch equals the binary coded decimal counter output logic coupled to said comparator for coupling a clocked output to said up-down counter that is equal to the incremental current changes.

4. Apparatus as set forth in claim 3 and further comprising a plurality of logic circuits, each of said logic circuits having a fundamental input switch and an incremental input switch for supplying current logic level outputs, the output of said latching circuit being coupled to each of said logic circuits for controlling the combination of the fundamental current signal and the incremental current signal, and an output of each of said logic circuits being coupled to said digital-analog converter for providing binary coded decimal logic signals thereto.

5. Apparatus as set forth in claim 4 wherein said firing circuit comprises a NAND gate latch having first and second inputs and an output; an OR gate having an output coupled to said first input; a NAND gate having a first input coupled to said latch output, a switch connected to a second input of said NAND gate for coupling a gating pulse thereto, and an output of said NAND gate being coupled as inputs to said converter for activating the converter; said OR gate having inputs coupled to said optical sensing means output and said first clock output; and a reset input coupled to said OR gate, said second NAND gate latching input being coupled in parallel with said reset input for initially setting said firing command circuit.

* * * * *